United States Patent [19]

Markov

[11] Patent Number: 4,703,040

[45] Date of Patent: Oct. 27, 1987

[54] TREATMENT OF ADULT RESPIRATORY DISTRESS SYNDROME (ARDS) USING FRUCTOSE DIPHOSPHATE (FDP)

[76] Inventor: Angel K. Markov, 5973 Hanging Moss Rd., Jackson, Miss. 39206

[21] Appl. No.: 785,778

[22] Filed: Oct. 8, 1985

Related U.S. Application Data

[63] Continuation-in-part of Ser. No. 719,504, Apr. 3, 1985, abandoned.

[51] Int. Cl.$^4$ .................. C07H 11/04; A61K 9/10; A61K 31/66
[52] U.S. Cl. ........................... 514/23; 536/117
[58] Field of Search ................ 536/117; 514/23

[56] References Cited

U.S. PATENT DOCUMENTS 4,530,902  7/1985  Perri et al. .................. 536/117

OTHER PUBLICATIONS

Melloni et al., "Chem. Abst." vol. 59, 1963, p. 6816 (f).
Markov et al., "American Heart Journal", vol. 100, No. 5, Nov. 1980, pp. 639-646.

Primary Examiner—Ronald W. Griffin
Attorney, Agent, or Firm—Pravel, Gambrell, Hewitt, Kimball & Krieger

[57] ABSTRACT

Fructose-1,6-diphosphate is administered intravenously to a mammalian subject experiencing adult respiratory distress syndrome (ARDS) in an amount sufficient to inhibit pulmonary microvascular damage.

6 Claims, 22 Drawing Figures

TREATMENT OF ADULT RESPIRATORY DISTRESS SYNDROME (ARDS) USING FRUCTOSE DIPHOSPHATE (FDP)

REFERENCE TO RELATED APPLICATION

This is a continuation-in-part of U.S. Ser. No. 719,504 filed Apr. 3, 1985, now abandoned by Angel K. Markov entitled "Method for Treating Adult Respiratory Distress Syndrome Using Fructose-1,6-Diphosphate."

The present invention relates to the treatment of adult respiratory distress syndrome after shock, sepsis, trauma and the like.

Acute pulmonary edema can be induced by intravenous or intraperitoneal injection of alpha-naphthylthiourea (ANTU). ANTU causes an increase in microvascular permeability, which leads to pulmonary edema. Investigators have quantitated the degree of edema, and described the morphological changes which accompany ANTU poisoning, the severity of which appear to be dose related.

It has been suggested that pulmonary edemagenic conditions are intimately coupled with the oxygen radical production associated with tissue damage, particularly that of the leukocytes. Upon challenge, the phagocytic cells undergo an increase in hexomonophosphate shunt (HMS) activity, an increase in oxygen uptake, an increase in superoxide ($O_2-$) production, and an increase in hydrogen peroxide ($H_{o2}$) production.

During the increase in HMS activity, the reduction potential of the cell is increased via increase in NADPH concentration (and, thereby $O_2-$ and $H_2O_2$ concentration). In the HMS, there are two steps which reduce NADP+: (1) oxidation of glucose 6-phosphate (G6P) with the enzyme glucose 6-phosphate dehydrogenase, and (2) oxidation of 6-phosphogluconate with the enzyme 6-phospho-gluconate dehydrogenase (PGDH). Fructose 1,6-diphosphate (FDP) has been shown to inhibit PGDH and in the resting phagocyte would serve to shut down HMS, increasing the flux of G6P into the glycolytic pathway.

Energy for phagocytosis has been shown to be derived almost exclusively from glycolysis. The concentration of FDP is dependent on the activity of phosphofructokinase I (PFK1) and the availability of its substrate fructose 6-phosphate. As the concentration of lactate increases (decreasing the pH) the activity of PFK1 decreases, thereby decreasing the concentration of FDP, and allowing the inflow of G6P into the HMS with the accompanying rise in NADPH concentration, which allows for the production of $O_2-$ and $H_2O_2$.

Histamine has also been suggested to be a possible mediator of pulmonary edema via an increase in vascular permeability. FDP has been shown to inhibit the release of histamine from mast cells.

This study was undertaken to examine the effects of FDP on the generation of pulmonary edema produced by ANTU. Treatment with FDP could serve three functions: (1) overcome the inhibition of PFK1, as FDP is a strong activator of this enzyme, (2) inhibit PGDH, thereby lowering the reduction potential, thus reducing the oxygen radical production, and possible tissue damage, and (3) inhibits histamine release from mast cells.

GENERAL DISCUSSION OF THE PRESENT INVENTION

Discussions of Adult Respiratory Distress Syndrome can be seen, for example, in the New England Journal of Medicine in an article entitled "Changing Concepts of Lung Injury and Repair," New England Journal of Medicine Vol. 306 No. 15, Apr. 15, 1982 at p. 900. Another article discussing ARDS can be found in the "Annals of Internal Medicine," May 1983 at p. 593 entitled "Adult Respiratory Distress Syndrome: Risk with Common Predispositions." A Baylor College of Medicine Cardiology Series dated 1984 (Vol. 7, No. 5) provides an article on Adult Respiratory Distress Syndrome by Gordon Bernard and Kenneth Brigham. Each of the above-discussed publications is incorporated herein by reference.

The Adult Respiratory Distress Syndrome (ARDS) representing pulmonary edema of non-cardiac origin can be observed following shock, sepsis, trauma and other insults on the pulmonary parenchyma causing alteration of capillary permeability. In treating patients in shock with Fructose 1-6 Diposphate (FDP), in those who had concomitantly ARDS I noted significant hemodynamic, radiographic, and pulmonary function improvement. In an effort to elicit the mechanism for this protective action of FDP in ARDS, I simulated the condition in 25 dogs by injecting them intravenously with alpha-Naphthylthiourea (ANTU). The animals were randomly assigned into two groups and 30 minutes after administration of ANTU, 12 were treated with FDP and those serving as controls received glucose solution in the same concentration and volume.

DETAILED DESCRIPTION OF THE PREFERRED EMBODIMENT

Mammalian subjects including ten mongrel dogs (weights = 14.0–32.0 Kg; mean = 19.5 kg) and fifteen greyhounds (17.7–32.2 kg; mean = 25.7 kg) of both sexes were anesthetized with Surital (thiamylal sodium, Parke-Davis, Morris Plains, N.J.) at 30 mg/kg thirty minutes after pre-anesthetic treatment with 10 mg acepromazine maleate. Dogs received additional 50 mg doses of Surital as needed. After induct of anesthesia, dogs were intubated and ventilated, when necessary, with a piston-type respiratory pump. Secured in the left decubitus position on the fluoroscopic table, catheters were percutaneously introduced into the left ventricle via the left external carotid; the pulmonary artery via the right jugular; the right femoral vein (for infusion and withdrawal); and the right femoral artery (for cardiac output measurements).

Pulmonary arterial, the left ventricular pressures were monitored throughout the experiment with Gould-Statham strain gauges interfaced with an Electronics for Medicine DR-8 recorder. EKG and heart rate were also monitored using the EM DR-8 recorder. Cardiac output was measured using Lexington Instruments Cardiac Output Computer and indocyanine green as indicator dye. Blood pH, $P_{CO_2}$ and $P_{O_2}$ were measured using a Radiometer/Copenhagen ABL3 OR ABL309 blood analyzer. ANTU [1-(1-naphthyl)-2-thiourea; Fairfield Chemical, Blythewood, SC] was prepared as a 1% suspension (w/v) in propylene glycol. FDP Esafosfina (TM); Biomedica Foscma; Rome, Italy) was prepared as a 10% solution (w/v) in sterile distilled $H_2O$). FDP and ANTU were prepared thirty minutes prior to administration.

After a thirty-minute control period, sixteen dogs received intravenous injections of ANTU at 5.0 mg/kg body weight and eight dogs at 10.0 mg/kg into the right femoral vein. Thirty minutes after administration of ANTU, the FDP 4reated goups (12 dogs; 8 having received ANTU at 5 mg/kg and 4 at 10 mg/kg) received 75 mg/kg FDP in slow I.V. bolus, then 600 mg/kg FDP at 191 mg/min. The control group (12 dogs; 8 having received ANTU at 5 mg/kg and 4 at 10 mg/kg) received normal saline at 0.75 ml/kg in slow I.V. bolus, then 6.0 ml/kg saline at 1.91 ml/min. Some received propylene glycol at 0.5 mg/kg, then, at 30 minutes received normal saline as per the control group. Hemodynamic measurements [means pulmonary arterial pressure (PaP), left ventricular pressure (LVP), cardiac output (CO), hemotocrit (Hct), and arterial and venous pH, $Pco_2$ and $Po_2$] were taken every 15 minutes for the first hour, then at 90, 120, 150, 180, and 240 minutes. At 4 hours the experiment was terminated, and the dogs were sacrificed with a KCl solution. Lungs were inflated (to remove blood), excised, weighed and examined microscopically for edema and hemorrhage. Biopsies (500-900 mg) were taken from the lungs, weighed and dried under vacuum for 48 hours for wet weight/dry weight (wet/dry). Significance of difference between groups were determined using Student's t test, and within groups using paired t tests. Pulmonary resistance ($R_p$) was calculated in CGS unit (dyne sec $cm^{-5}$) with the equation: $R_p = [79.98 \times Pap$ (mm hg)]/[CO (L/min)].

At 4 hours the dogs were killed, the lungs exsanguinated and wet and dry weights recorded. The pulmonary pressure in the dogs treated with FDP remained unchanged while in those serving as controls increased from $12.9 + 2.4$ to $21.8 + 3.14$ mm Hg<(p 0.001). There were no differences between the two groups in left ventricular diastolic and arterial pressures, and cardiac outputs; however, pulmonary resistances in the dogs receiving glucose was significantly higher ($p < 0.001$). Lung to body weight (gm/kg) ratio for the FDP group was $9.83 + 0.684$ and for the controls $16.7 + 0.990$ ($p < 0.001$). The wet to dry lung weight ratio (gm/kg) for the treated dogs was $4.32 + 0.17$ and for those receiving glucose $6.18 + 0.396$ ($p < 0.001$). Nine patients in severe shock who had ARDS received 75 mg/kg of FDP (Esafosfina (TM)) as 10% solution every six hours. Hemodynamic and pulmonary function parameters were measured prior to and post FDP administration. FDP administration caused immediate and significant increase in arterial pressure ($p < 0.001$), cardiac output ($p < 0.001$), arterial $pO_2$ ($p < 0.001$), while lowering pulmonary arterial pressure and resistance ($p < 0.00$) and $p < 0.001$ respectively), heart rate ($p < 0.025$), arterial $pCO_2$)$p < 0.025$) and pulmonary wedge pressure ($p < 0.001$). These changes were evident immediately after FDP administration and persisted as long as the FDP was administered at the specified regiment. In most cases, vasopressor therapy was discontinued and $FiO_2$ and PEEP were decreased after FDP administration. The experimental data and clinical observation indicates that FDP is useful in the treatment of ARDS and supports the contention that FDP attenuates pulmonary microvascular damage by inhibiting histamine release from the mast cells in dose related fashion and by inactivation of the hexose monophosphate shunt in the neutrophils which generates free radicals (superoxides and peroxides). In the latter case, FDP directly inhibits the activity of 6-phosphogluconate dehydrogenase.

Figure 3:
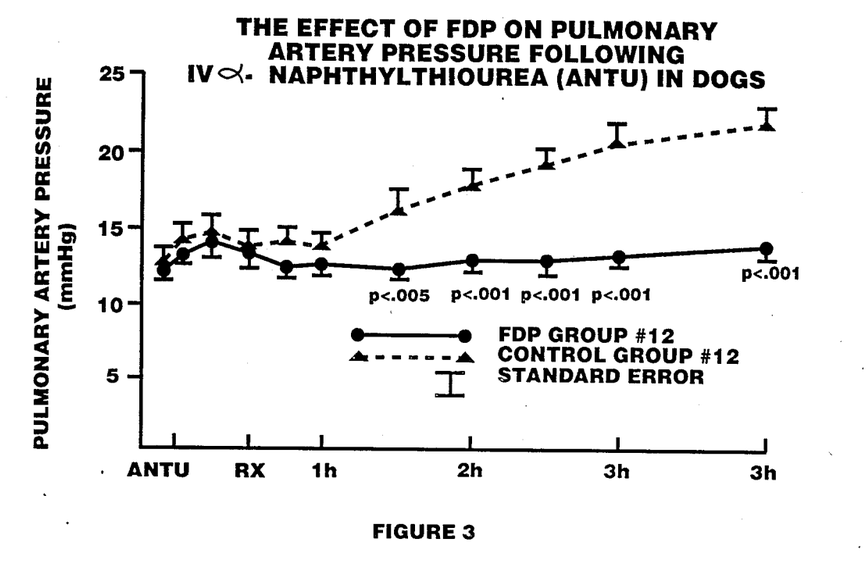

FIG. 3 represents the pulmonary pressure changes in dogs who are injected with alpha-Naphthylthiourea (ANTU). This agent produces conditions similar to ARDS in animal model. As you see in FIG. 3, the Fructose Di-phosphate is administered 30 minutes after the injection of the alpha-Naphthylthiourea and this Fructose Di-phosphate prevents an increase in the pulmonary pressure.

Figure 2:
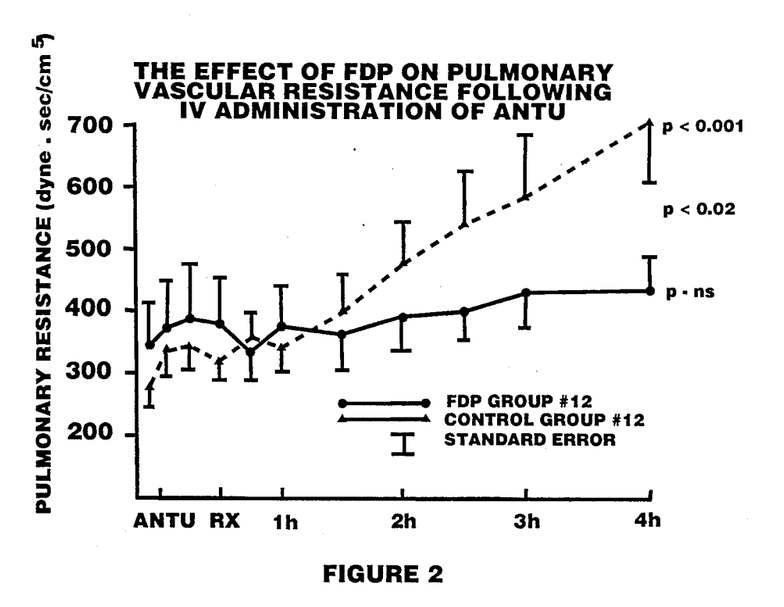

FIG. 2 represents the pulmonary vascular resistance in dogs injected with ANTU. The pulmonary resistance increased significantly (p 0.001) in the dogs treated with saline, while in those receiving FDP the pulmonary resistance did not change significantly from control values.

Figure 1:
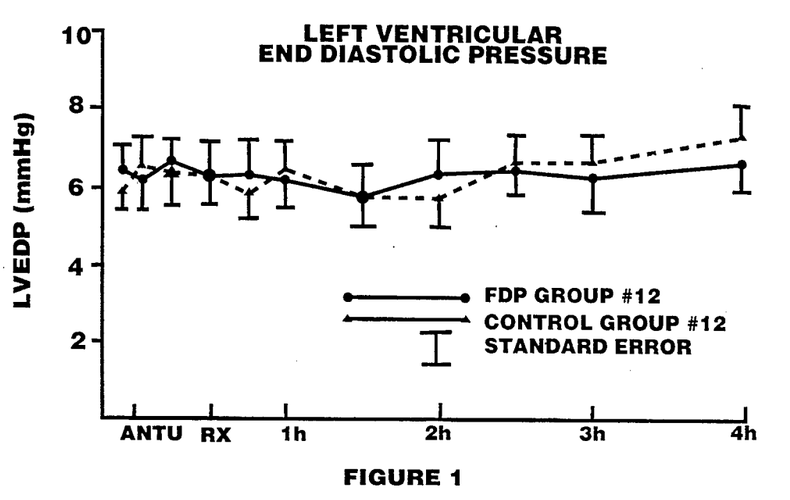

FIG. 1 is the left ventricular end diastolic pressure which is in normal limits. This is shown because if there is an increase in it (above 28 mm Hg), pulmonary edema will occur, but it will be of cardiogenic origin. Pulmonary edema is defined as accumulation of fluid (water) in the lungs (alveolic, parenchyma, etc.). Such elevated left ventricular pressures can be seen in patients with cardiac failure, myocardial infarction or primary myocardial disease comprising the ventricular function; conditions which will produce pulmonary edema. This finding substantiates the fact that the ventricular function was normal and therefore the edema formed by ANTU is not from a cardiogenic origin.

Figure 4:
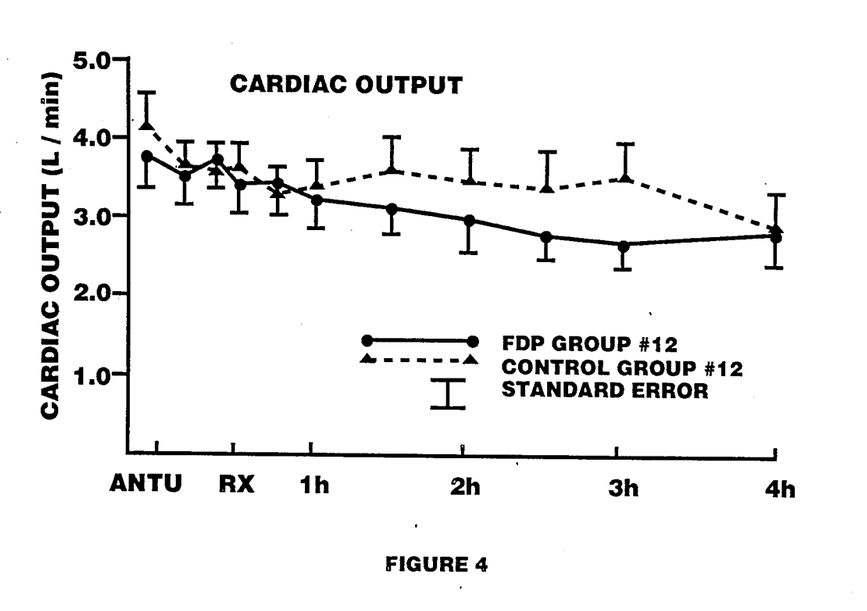
Figure 5:
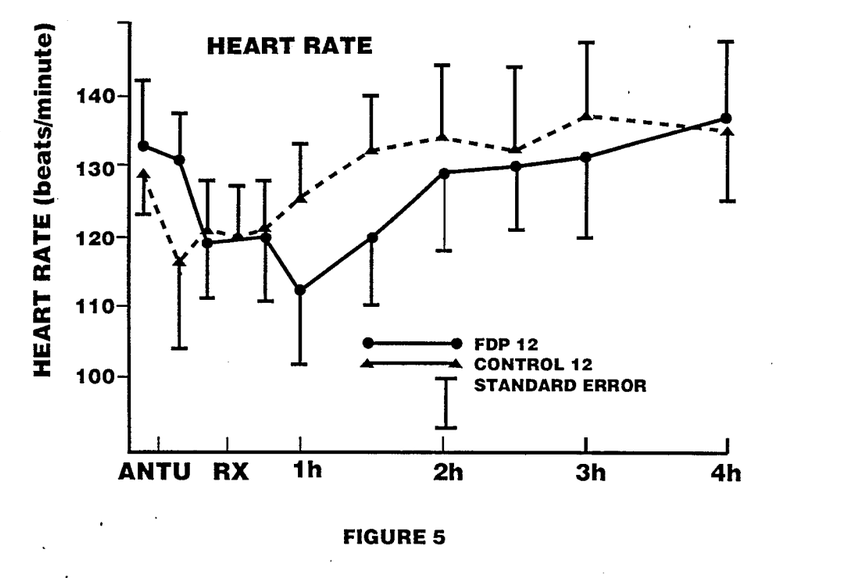
Figure 6:
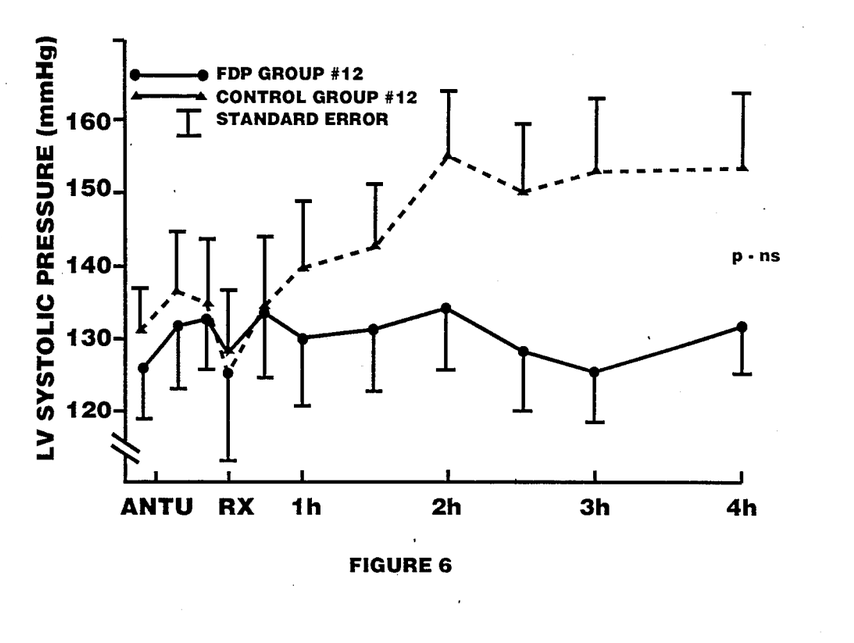

FIG. 4 shows that there was no difference in the cardiac output between the controls and those treated with FDP. Thus, the ANTU did not compromise the heart functions. There was no significant difference in the heart rate in FIG. 1 between the controls and the FDP treated dogs. FIG. 6 shows there was no significant difference in the left ventricular pressures between the two groups of dogs.

Figure 7:
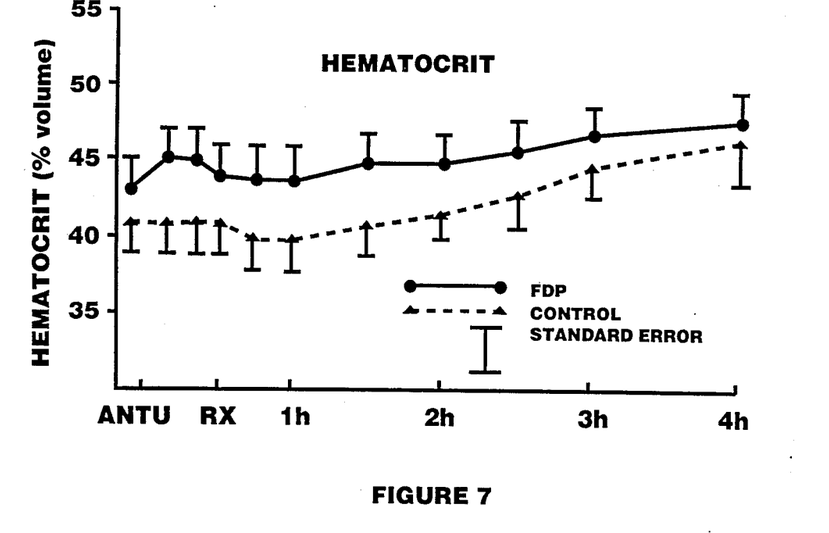
Figure 8:
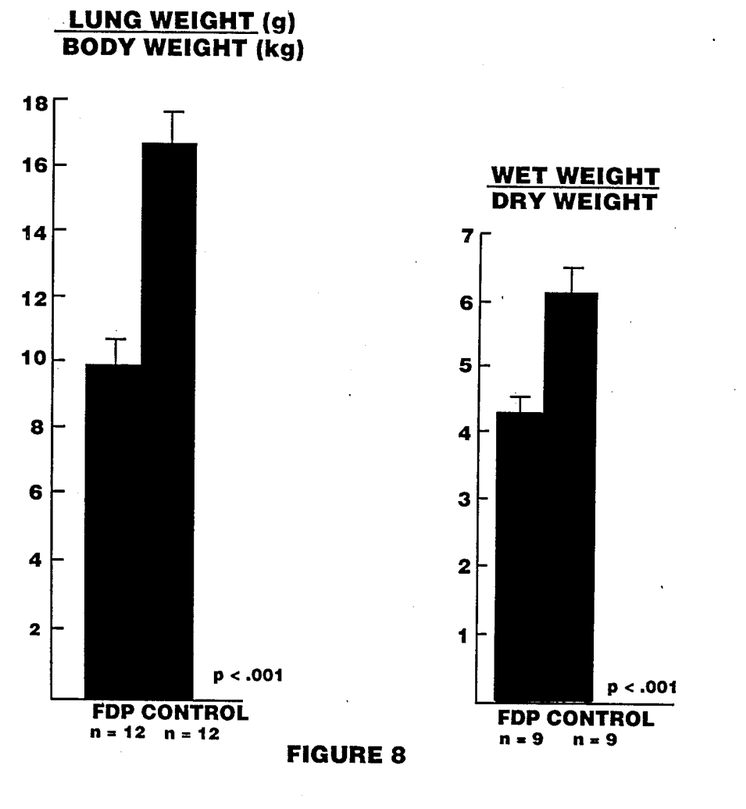

FIG. 7 shows that the Hematocrit was no different between the FDP treated and control animals, and FIG. 8 (which is one of the most important findings in this study), illustrates that the lungs on the dogs treated with FDP had a normal lung to body weight ratio as well as wet to dry ratio. That is to say, no water was accumulated in the FDP treated dog after an injection of alpha-Naphthyltiourea, confirming our hypothesis that the agent prevents non-cardiogenic pulmonary edema which is comparable with the human ARDS patient.

Figure 9:
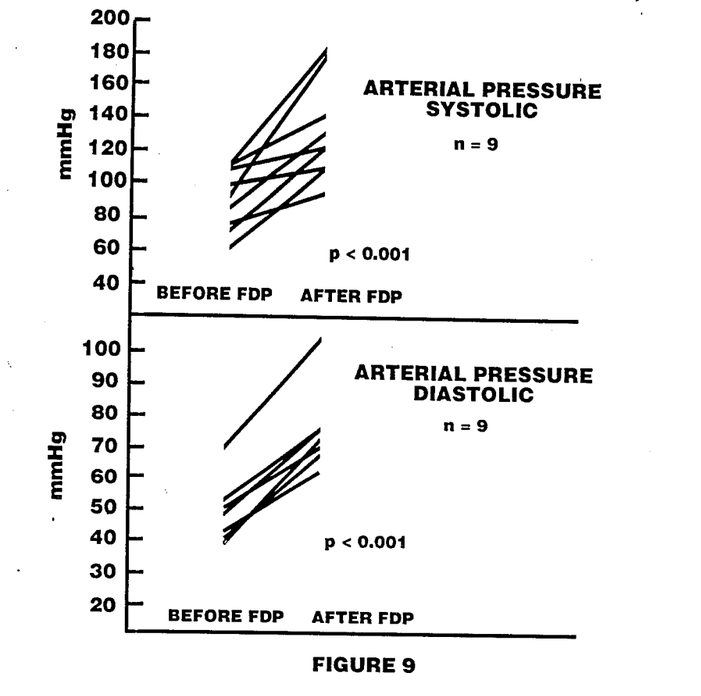
Figure 10:
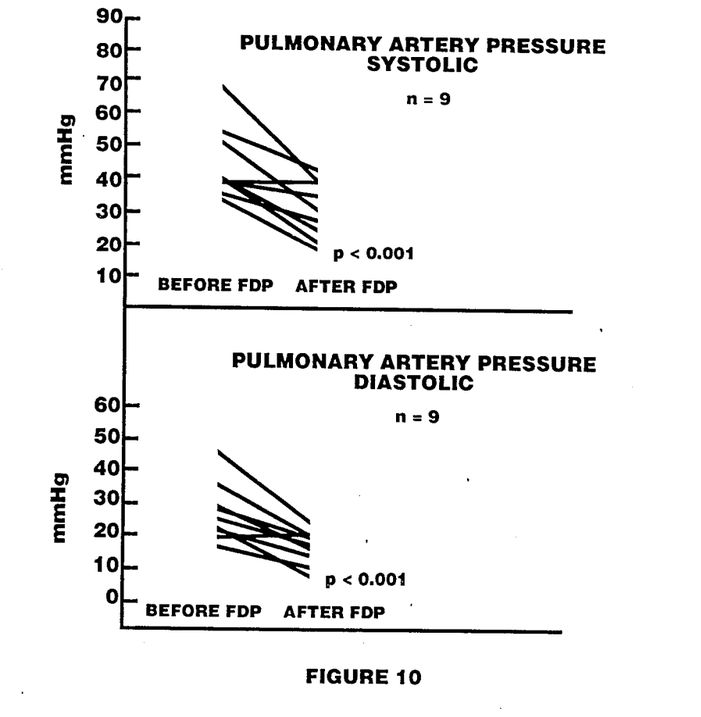

FIG. 9 represents the Systolic and Diastolic pressures of nine patients which were in shock and were treated with FDP. These patients happened to have ARDS. The shock was from sepsis, trauma and other causes. As you can see, FDP improved the arterial pressures (both Systolic and Diastolic) significantly. The pulmonary artery pressures on these patients were obviously elevated (as seen in ARDS) and after the administration of the FDP it declined significantly (see FIG. 10).

Figure 11:
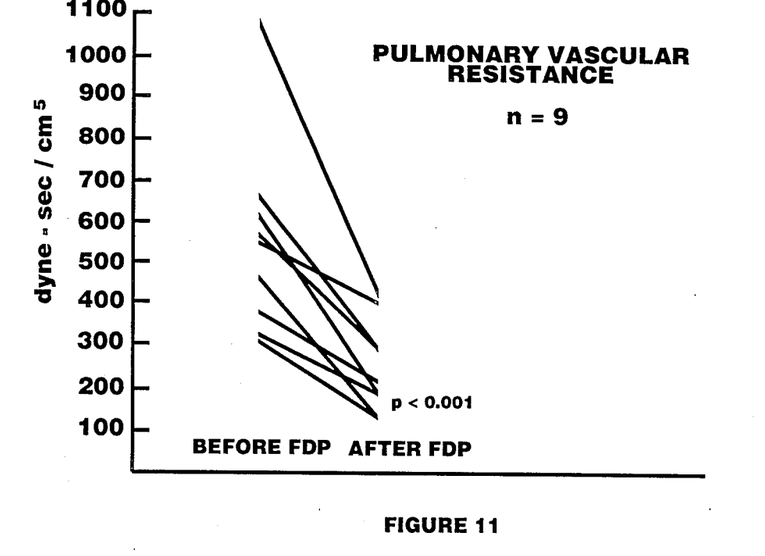
Figure 12:
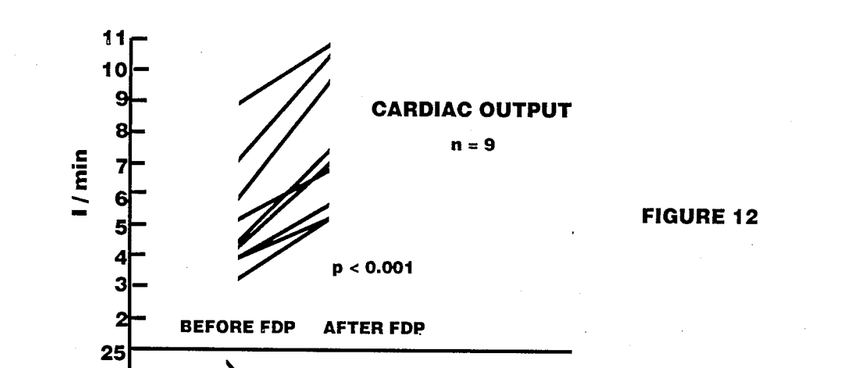

FIG. 11 clearly shows how FDP decreased the pulmonary vascular resistance in all of the patients with ARDS. FIG. 12 shows that cardiac output improved in all of these patients. Those who had a very high cardiac output (normally seen in patients in septic shock) was also increased.

Figure 13:
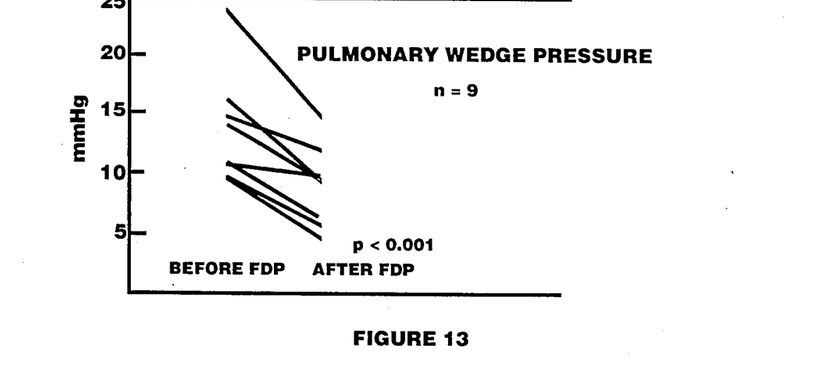
Figure 14:
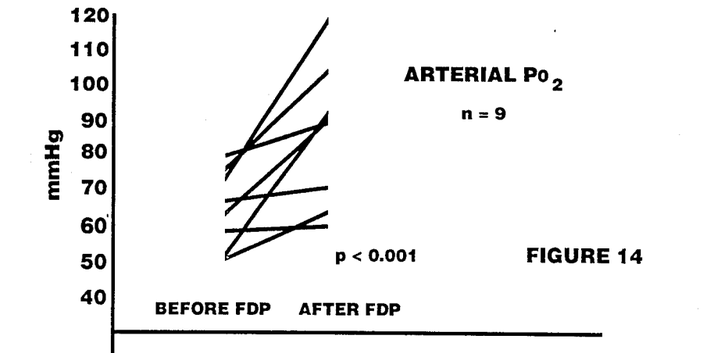

FIG. 13 demonstrates that the wedge pressure or the left ventricular pressure were in the high normal range except for one patient which was pathological (about 27 mm Hg). That is to indicate that these patients did not have a pulmonary edema from a cardiogenic origin, perhaps except for one, and after the injection of FDP, the pulmonary wedge pressure declined significantly attaining near normal values. The condition ARDs manifests itself by pulmonary edema of non-cardiogenic origin and arterial hypoxemia. That is to say, the oxygen in the arterial blood is very low and after the administration of FDP (see FIG. 14), the arterial oxygen partial pressure increased significantly higher after those patients received the FDP.

FIGS. 1, 2, 3, 4, 5, 6, 7 and 8 are in dogs. The remaining figures are all human patients (i.e., FIGS. 9 through 22).

Figure 15:
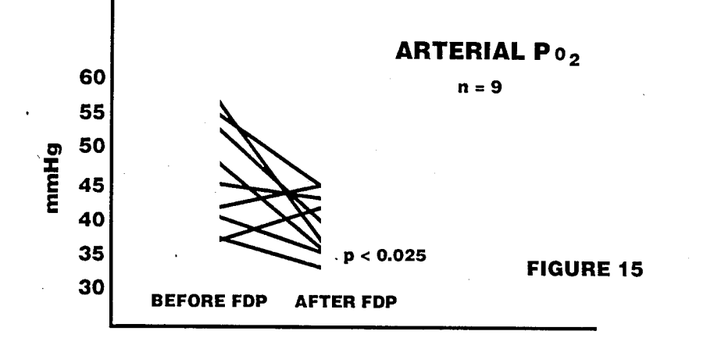

In FIG. 15, those patients that had the reverse gases $PCO_2$ in the arterial blood (i.e., the carbondioxide was higher than the oxygen) and the FDP treatment corrected these abnormalities.

Figure 16:
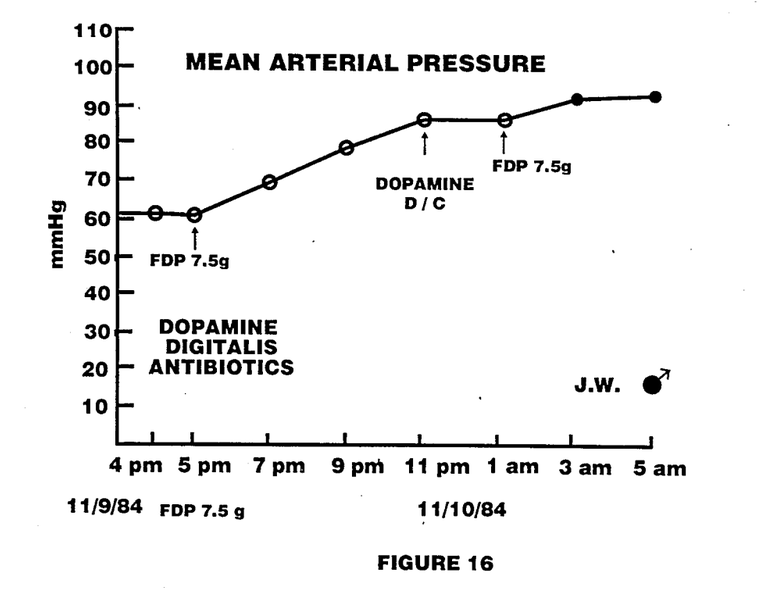

FIG. 16 gives the response of a single patient in the time span of six hours between two administrations of FDP. FIG. 16 represents the response of his arterial pressure to FDP administration (which was very low, sine he was in shock). We were able to discontinue the dopamine (a drug used to maintain blood pressure in patients in shock). In the same patient following FDP treatment, the arterial $PO_2$ increased immediately from 70 to 90 millimeters of mercury. This enabled us to decrease the oxygen delivered by the respirator (percentage of oxygen). By 3:00 a.m. that morning the patient had a 120 mm Hg at 35% percent of ogygen (see FIG. 21).

Figure 17:
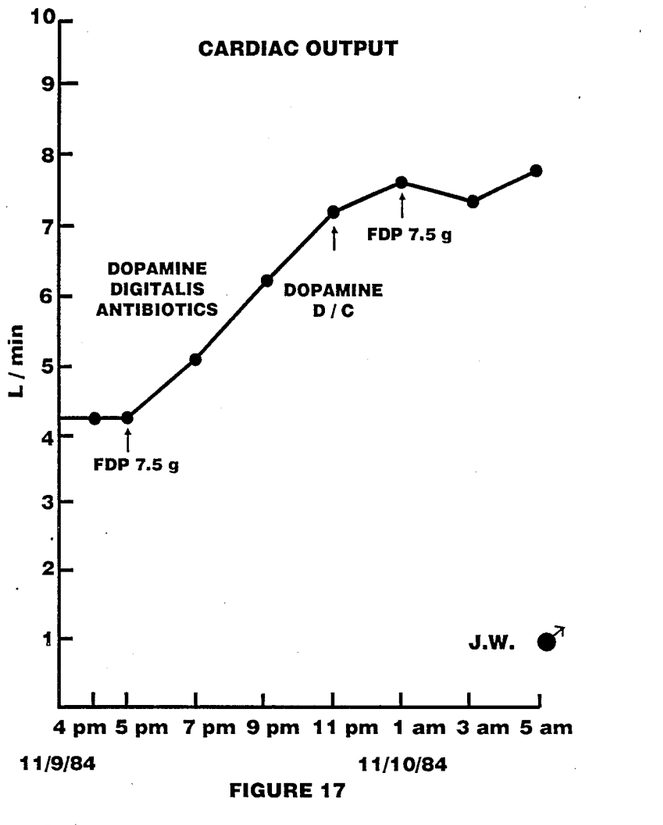
Figure 18:
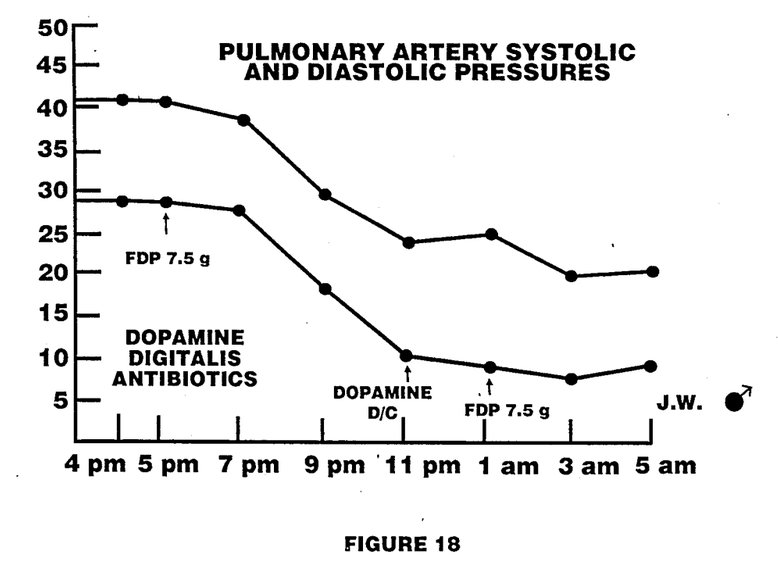

FIG. 17 shows a response of the cardiac output. You can see it doubled after the administration of FDP. In FIG. 18, the pulmonary pressure was elevated (above normal) and after the administration of FDP the pressure declined back to normal limits.

Figure 19:
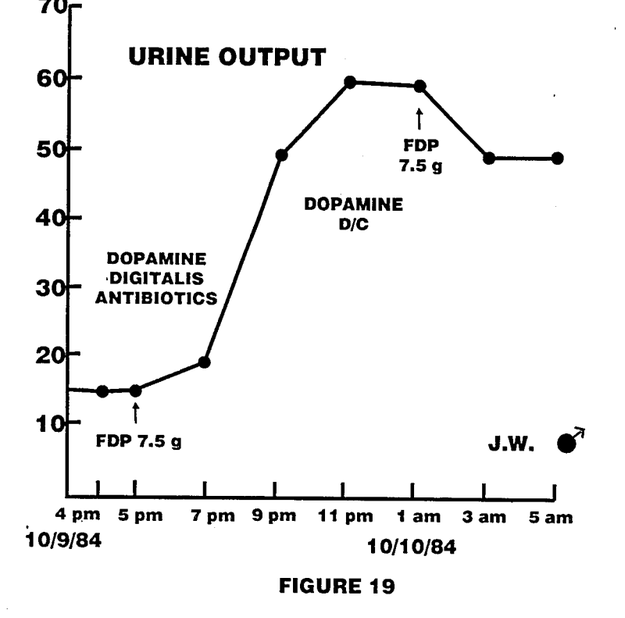
Figure 20:
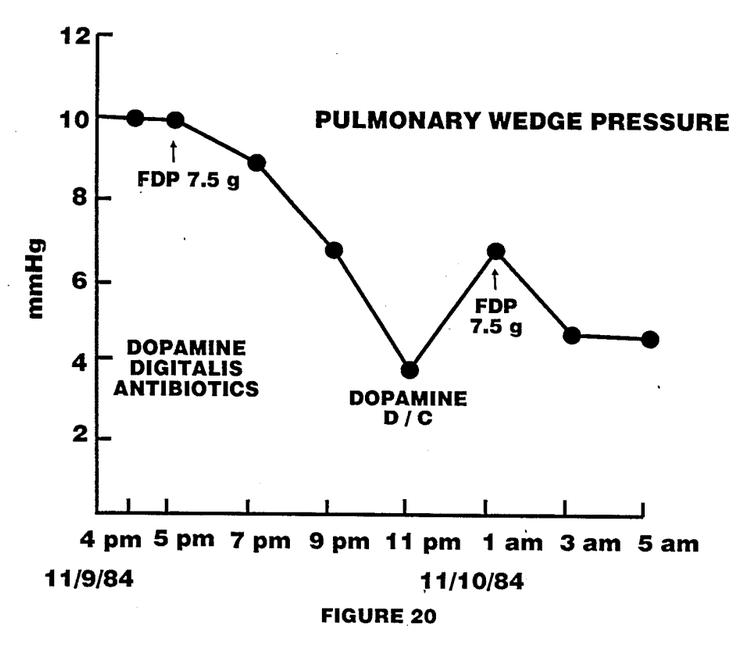
Figure 21:
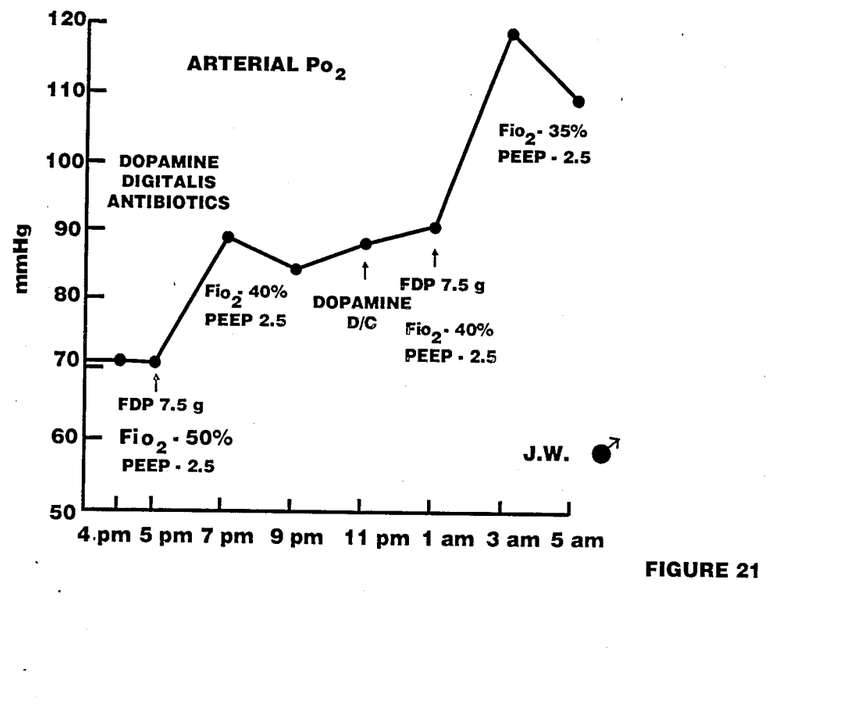

FIG. 19 shows the patient had a marginal renal function and following administration of FDP, his urinary output increased from 16 milliliters per hour up to 60 milliliters per hour. Wedge pressure was normal in this patient, which substantiates that the pulmonary edema or ARDs was not from cardiogenic origin. The genesis of ARDS in man generally is attributed to accumulation and sequestration of neutrophils in the lungs following direct or indirect injury of the lungs. The neutrophils damage the pulmonary capillary (blood vessels) by releasing toxic oxygen redicals $O_2$ $H_2$ $O_2$ OH, causing fluid to leak from the capillary into the lung alveolic and parenchyma.

Figure 22:
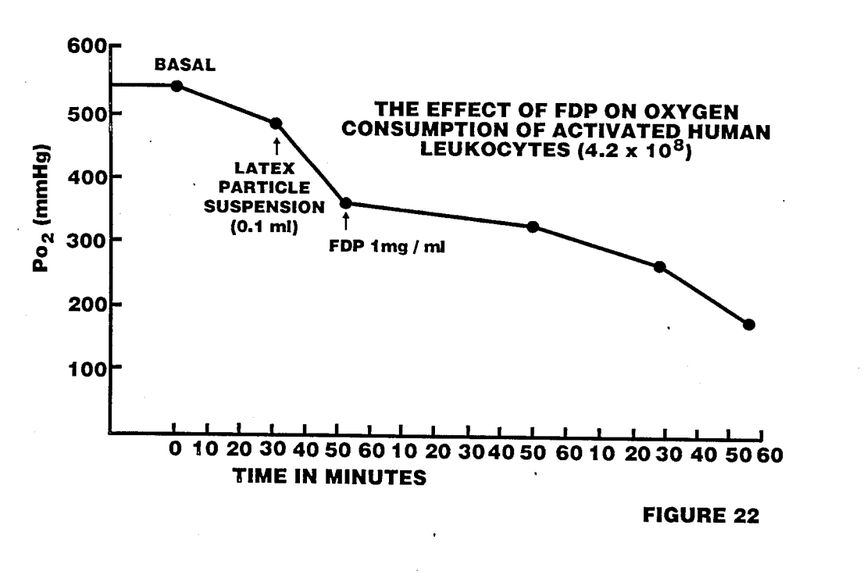

FIG. 22 gives direct support of the hypothesis that FDP inhibits free radical formation by the Leukocytes (neutrophils). As approximately 98% of the oxygen used by stimulated human Leukocytes and as well as dog Leukocytes (known as respiratory burst) is consumed to convert glucose to a pentose and $CO_2$, concomitantly free radicals such as single oxygen, ($O_2$) hydrogen peroxide ($H_2O_2$) and others are formed which are very toxic for the pulmonary parenchyma and capillaries. Most of the authors believe that activated Neutrophis cause the damage in the lung during the condition called ARDs. Here we have demonstrated that in this vitro study, FDP inhibits completely the respiratory burst. This has been confirmed in vitro on animal models and in vitro on human and dog neutrophis.

The foregoing description of the invention is illustrative and explanatory thereof, and various changes in the size, shape and materials, as well as in the details of the illustrated construction may be made without departing from the spirit of the invention.

I claim:

1. A method for treating a mammalian subject experiencing adult respiratory distress syndrome (ARDS) comprising;
   administering intravenously to the subject fructose-1,6-diphosphate in an amount sufficient to inhibit pulmonary microvascular damage.

2. The method of claim 1, wherein administration is made as a single dose in an amount of 75 mg/kg subject body weight.

3. The method of claim 1, wherein administration is by intravenous infusion drip.

4. A method for treating a mammalian subject experiencing adult respiratory distress syndrome comprising:
   administering intravenously to the subject, fructose-1,6-diphosphate in an amount sufficient to inhibit pulmonary microvascular damage wherein administration is made as a single dose in an amount of 1–500 mg/kg subject body weight for an adult.

5. The method of claim 4, wherein administration is by intravenous infusion drip.

6. A method for treating a mammalian subject experiencing Adult Respiratory Distress Syndrome, comprising the steps of:
   intravenous administration to the subject of fructose-1,6-diphosphate in an amount sufficient to inhibit pulmonary microvascular damage and noncardiogenic pulmonary edema by inhibiting the formation of toxic oxygen free radicals generated by the aggregated neutrophils in the lung.

* * * * *